United States Patent
Uflacker

(10) Patent No.: US 6,796,989 B2
(45) Date of Patent: Sep. 28, 2004

(54) INTRALUMINAL CUTTER FOR VASCULAR, BILIARY AND OTHER APPLICATIONS

(76) Inventor: Renan Uflacker, 548 Overseer's Retreat, Mt. Pleasant, SC (US) 29464

(*) Notice: Subject to any disclaimer, the term of this patent is extended or adjusted under 35 U.S.C. 154(b) by 0 days.

(21) Appl. No.: 10/139,670

(22) Filed: May 6, 2002

(65) Prior Publication Data

US 2003/0208215 A1 Nov. 6, 2003

(51) Int. Cl.⁷ ............................................. A61B 17/22
(52) U.S. Cl. ...................................... 606/159; 606/167
(58) Field of Search ......................... 604/22, 156, 158; 606/159, 167

(56) References Cited

U.S. PATENT DOCUMENTS

| | | | |
|---|---|---|---|
| 3,998,222 A | * 12/1976 | Shihata | 128/214 R |
| 4,347,846 A | 9/1982 | Dormia | |
| 4,612,931 A | 9/1986 | Dormia | |
| 4,921,484 A | 5/1990 | Hillstead | |
| 4,926,858 A | 5/1990 | Gifford, III et al. | |
| 4,950,277 A | 8/1990 | Farr | |
| 4,966,604 A | 10/1990 | Reiss | |
| 4,990,134 A | 2/1991 | Auth | |
| 5,009,659 A | 4/1991 | Hamlin et al. | |
| 5,030,201 A | 7/1991 | Palestrant | |
| 5,034,001 A | 7/1991 | Garrison et al. | |
| 5,041,082 A | 8/1991 | Shiber | |
| 5,100,425 A | 3/1992 | Fischell et al. | |
| 5,154,724 A | 10/1992 | Andrews | |
| 5,176,693 A | 1/1993 | Pannek, Jr. | |
| 5,217,474 A | 6/1993 | Zacca et al. | |
| 5,224,945 A | 7/1993 | Pannek, Jr. | |
| 5,250,060 A | 10/1993 | Carbo et al. | |
| 5,314,407 A | 5/1994 | Auth et al. | |
| 5,314,438 A | 5/1994 | Shturman | |
| 5,571,168 A | * 11/1996 | Toro | 623/1 |
| 5,766,191 A | 6/1998 | Trerotola | |
| 5,897,567 A | 4/1999 | Ressemann et al. | |
| 5,902,263 A | 5/1999 | Patterson et al. | |
| 5,925,054 A | * 7/1999 | Taylor et al. | 606/153 |
| 5,941,869 A | 8/1999 | Patterson et al. | |
| 6,010,522 A | 1/2000 | Barbut et al. | |
| 6,090,115 A | * 7/2000 | Beyar et al. | 606/113 |
| 6,183,482 B1 | 2/2001 | Bates et al. | |
| 6,190,394 B1 | 2/2001 | Lind et al. | |

* cited by examiner

Primary Examiner—Vy Bui
Assistant Examiner—Charles H. Sam
(74) Attorney, Agent, or Firm—Hodgson Russ LLP

(57) ABSTRACT

An intraluminal cutter having an expandable, rotary cutter with a plurality of cutting blades designed to cut and remove tissue proliferation within a stent and also to reopen stents. The intraluminal cutter is placed within the lumen of the clogged stent and expanded. By rotary movement of the expanded cutter blades, the device cuts and removes the material within the lumen. It is emphasized that this abstract is provided to comply with the rules requiring an abstract that will allow a searcher or other reader to quickly ascertain the subject matter of the technical disclosure. It is submitted with the understanding that it will not be used to limit the scope or meaning of the claims. 37 C.F.R. 1.72(b).

6 Claims, 6 Drawing Sheets

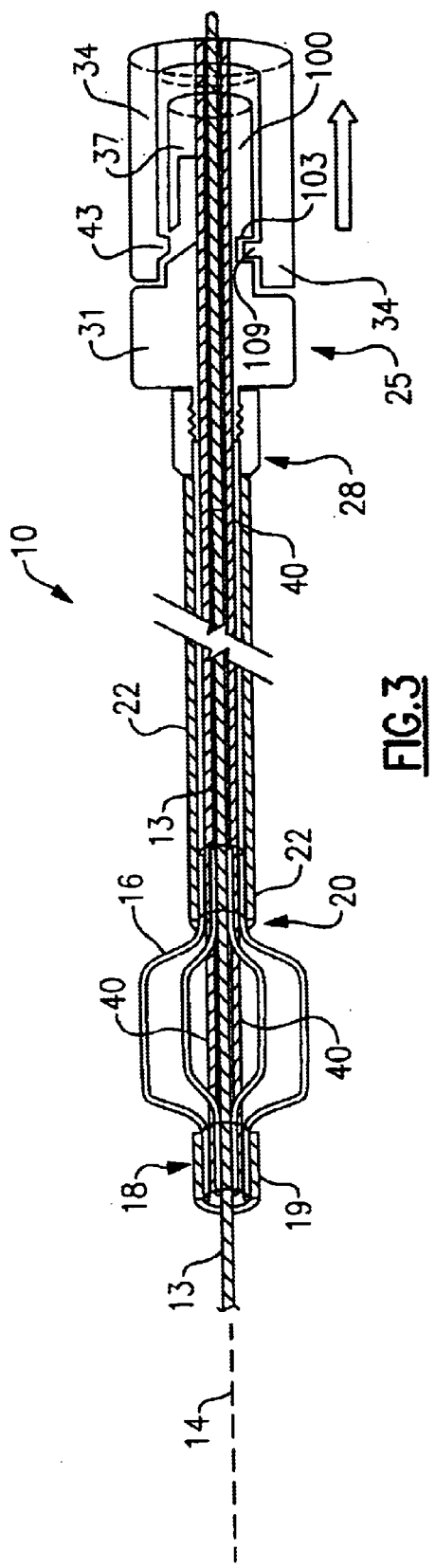
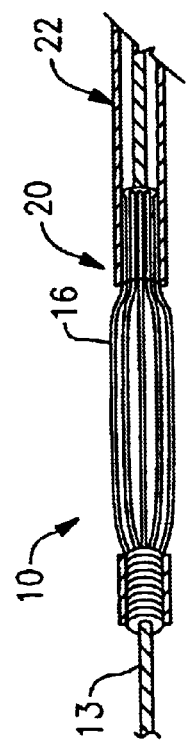
FIG.3
FIG.4

INTRALUMINAL CUTTER FOR VASCULAR, BILIARY AND OTHER APPLICATIONS

FIELD OF THE INVENTION

The present invention pertains to an intraluminal cutter for trimming ingrowth from the inside of stents or other shunts.

BACKGROUND OF THE INVENTION

Current ways of dealing with tumor ingrowth into a lumen of a metallic stent include putting a second stent within the stent, or placing a catheter across or placing a covered stent within the stent. The covered stents are not readily available in the United States, and may become crimped by the tumor mass within the primary stent. Cleaning the lumen of the stent from the tumoral ingrowth may be a better alternative, even when a second stent is planned to be inserted.

Accordingly, there is a need for intraluminal cutters for many applications including, but not limited to, biliary stents and TIPS shunts.

SUMMARY OF THE INVENTION

The present invention meets the above-described need by providing an expandable, rotary cutter having a plurality of cutting blades designed to cut and remove tissue proliferation within stents, and reopen stents. The intraluminal cutter is placed within the lumen of the clogged stent and expanded. By rotary movement of the expanded cutter blades, the device cuts and removes the material within the lumen. Cleaning out the lumen of the stent/shunt with the cutter is superior to prior art methods and devices for reintroducing flow through the stent.

These and other features and advantages of the present invention will become more apparent to those skilled in the art by reference to the following description.

BRIEF DESCRIPTION OF THE DRAWINGS

The invention is illustrated in the drawings in which like reference characters designate the same or similar parts throughout the figures of which:

FIG. 3 is a sectioned side elevation of the intraluminal cutter of the present invention;

FIG. 4 is a partial view of the intraluminal cutter, showing the rotary cutter blades in the contracted or closed position;

DETAILED DESCRIPTION OF THE INVENTION

The present invention is disclosed in connection with biliary stents and TIPS shunts, however, it is to be understood that the present invention may be used for stents and shunts used in other vessels.

Figure 1A:
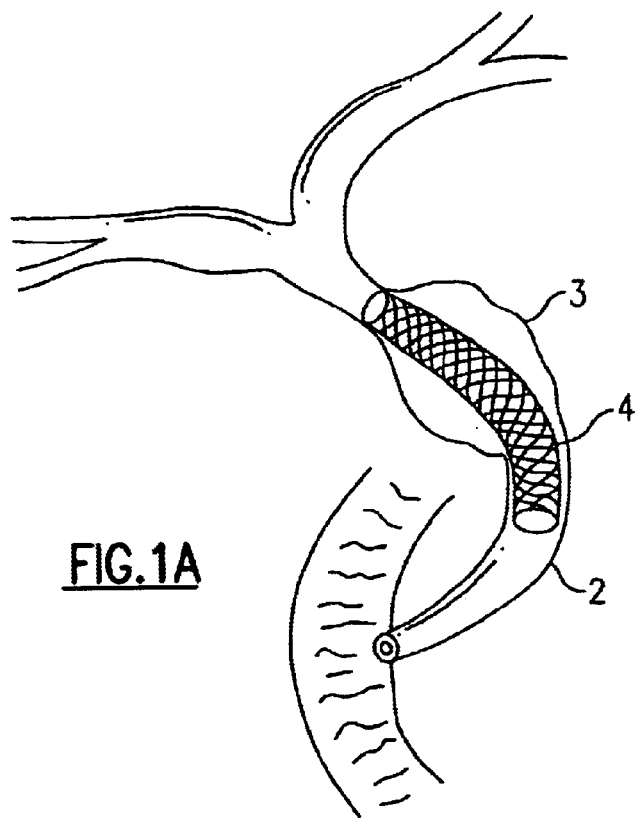
FIG. 1A shows a bile duct tumor with a metal stent within the tumor.
Figure 1B:
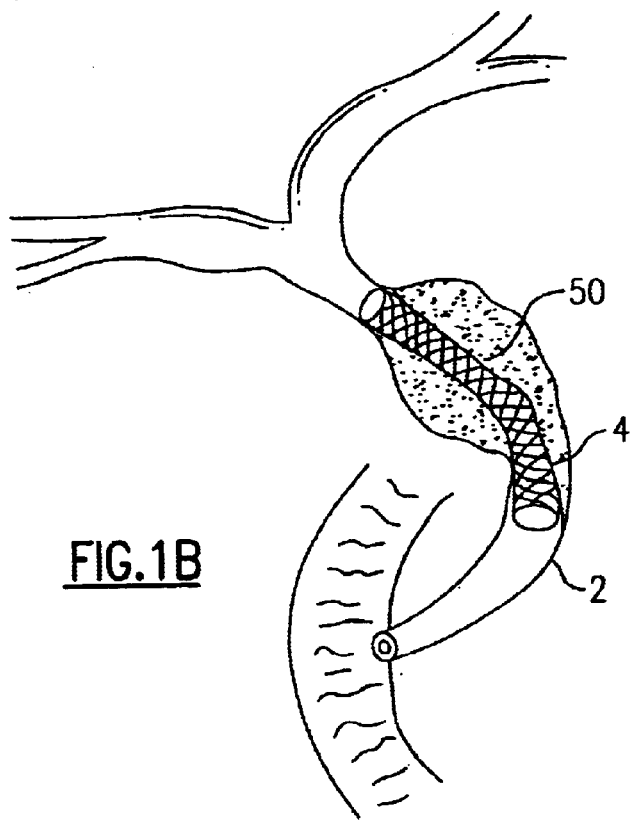
FIG. 1B shows the bile duct tumor of FIG. 1A with the metal stent within the tumor but with ingrowth within the lumen of the stent.
Figure 1C:
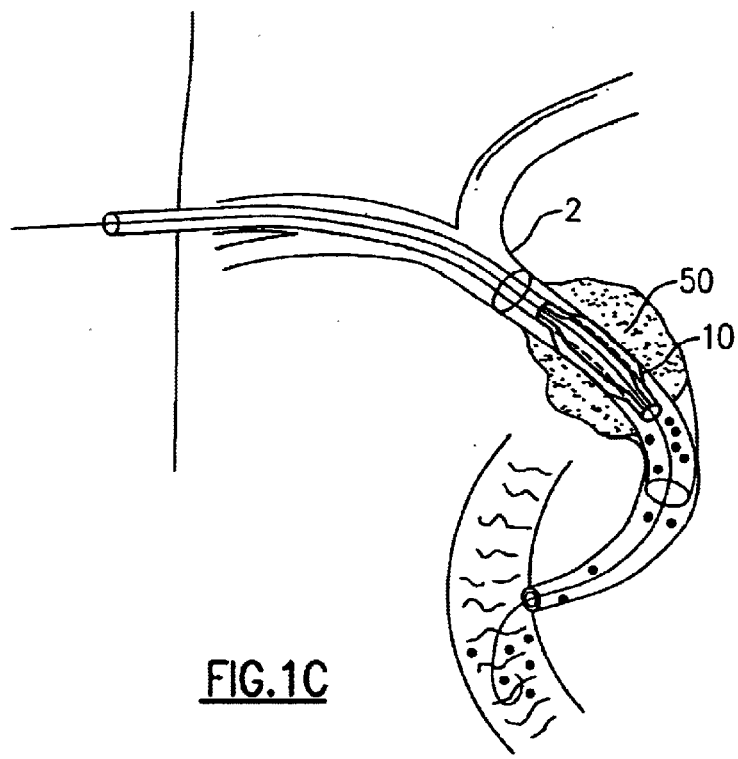
FIG. 1C shows the intraluminal cutter in action, through a percutaneous access, debulking the tumor ingrowth with the lumen of the stent, with particles of removed tissue migrating distally.

Referring to FIGS. 1A–C, palliation of obstructive, unresectable tumors causing occlusion of the bile flow through the bile ducts 2, is a major indication for percutaneous biliary drainage in patients with malignant lesions 3. Biliary drainage is initially performed with a catheter, followed by an endoprosthesis implant, if indicated. The rationale for using a catheter or metal stent is to improve bile flow and counteract the complications caused by the biliary obstructive process and cholestasis (stasis of bile within the liver). Major symptoms and complications of biliary duct obstruction include jaundice (accumulation of bile salts in the body), pain, pruritis, anorexia and weight loss.

Biliary catheters are effective drainage devices, but are left hanging out of the patient skin, connected or not to a bag. Catheters need to be exchanged every four to six weeks, because they become clogged up by bile debris and accumulation of bile salts and proteins in the lumen and walls. Catheters are, therefore, considered to be temporary means of bile duct drainage.

The biliary endoprosthesis or stents 4 are designed to be more comfortable to the patients, do not connect with the exterior and offer a much larger lumen for internal biliary drainage. The durability of a metallic stent is certainly longer than a plastic internal stent or a percutaneous drainage catheter, however, it is still limited by the almost certain tumor ingrowth through the wire mesh of the stent walls.

Turning to FIGS. 2A–D, another common problem related to stent obstruction is encountered in the TIPS procedure. TIPS (transjugular intrahepatic portosystemic shunt) in which a wire mesh stent is implanted via catheter between the portal and hepatic venous circulation, creating a new vessel within the liver, is the most recent development in the management of portal hypertension. The shunt, similar to the surgical one, relieves high portal vein pressure caused by progressive occlusion of portal vessels at the level of microcirculation, in patients with advanced liver cirrhosis. In the past, the only option was a surgical bypass that has high morbidity and mortality risks and led to a long inpatient recovery. In addition to these problems, the surgical operation was so extensive, it was rarely appropriate for the sickest patients.

In contrast, TIPS has proven to be a relatively safe, well-tolerated and reliable means of palliation for portal hypertension, and it can be offered to a much wider range of patients. The typical patient is admitted with upper GI bleeding from varices that develop when circulation in their cirrhotic liver shuts down and the pressure in the portal vein goes up. Although the bleeding can be stopped with esophageal balloon catheters and endoscopic sclerosis of varices, that does not treat the portal hypertension that is causing the bleeding. The procedure is especially useful in transplant centers where a number of patients are waiting in line for an organ for transplantation. Patients that can benefit from the TIPS procedure are liver transplant candidates, reducing the complications of portal hypertension, such as controlling variceal bleeding, development of ascites and encephalopathy, gaining time as they wait for an available organ.

The TIPS procedure can be briefly described as follows. After a guide wire has been passed from the jugular vein through the vena cava and into the hepatic vein 6, a needle-tipped catheter is used to pierce the hepatic vessel wall 7 punch through about a few centimeters of liver tissue and enter the portal vein 8. Pressure measurements are made in both veins to provide a baseline for evaluating gradient changes after stent placement. A guide wire is advanced into the portal vein. The catheter is advanced over the wire.

Following balloon dilation of the new passage, a stainless steel mesh stent 9 is expanded into the opening. Contrast dye is injected to confirm patency and check for proper positioning of the stent, and the new pressure gradient is recorded for comparison with the baseline.

The new mesh stent used for the shunt may develop occlusion in 20% to 50% of the patients, which will require a second intervention to open. Most commonly the occlusion will be caused by ingrowth of the tissue along the inner surface of the shunt. Interventions to open the stent are usually performed with balloon angioplasty, and new stent placement. A new way to clean the lumen of the TIPS shunt would be to remove the tissue ingrowth within the stent with the cutter of the present invention, rather than perform a balloon angioplasty or new stent placement.

Figure 2A:
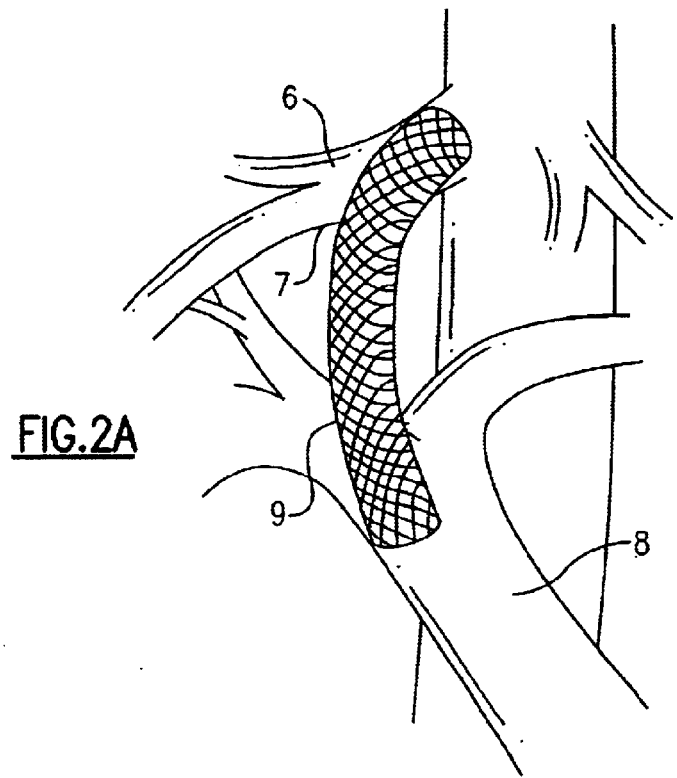
FIG. 2A shows a metal stent after removal of the guide wire.
Figure 2B:
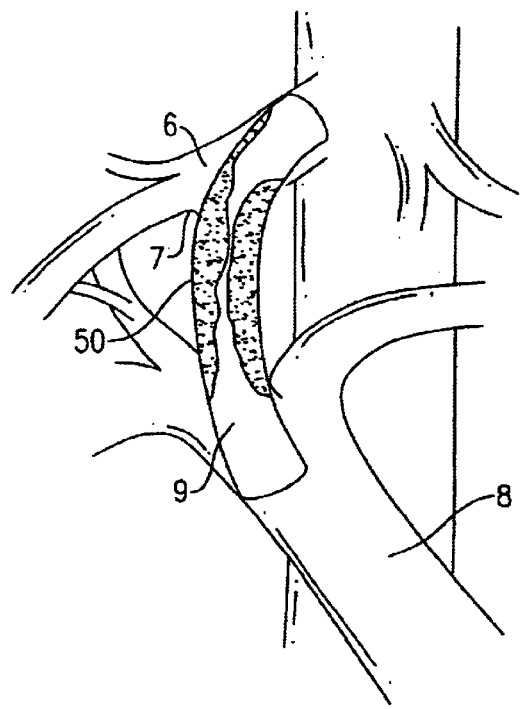
FIG. 2B depicts ingrowth of tissue along the inner surface of the shunt.
Figure 2C:
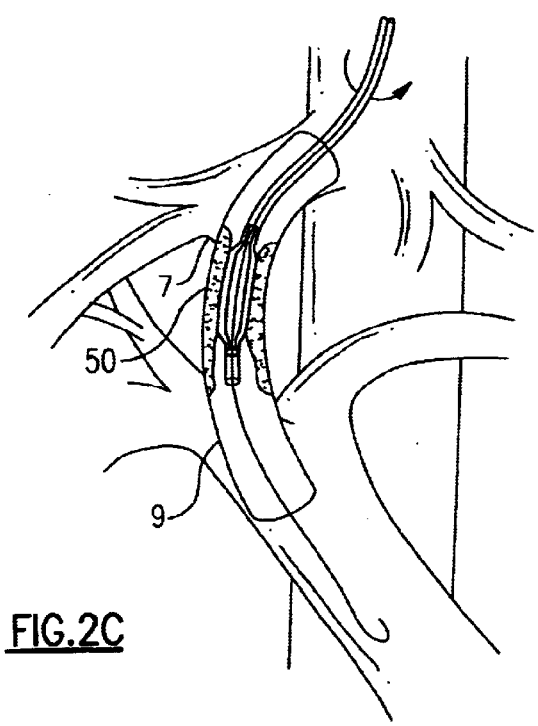
FIG. 2C shows balloon angioplasty in the area of the ingrowth tissue.
Figure 2D:
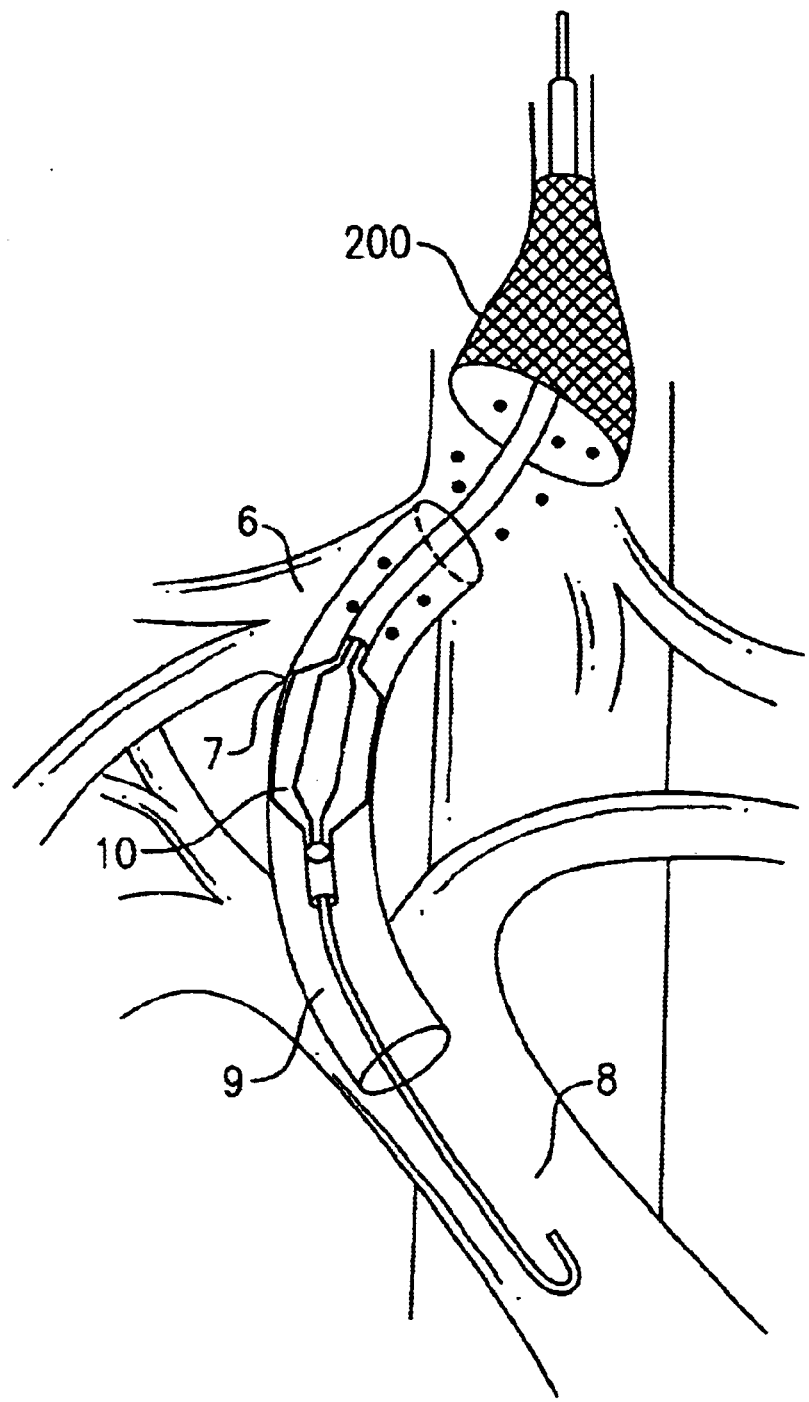
FIG. 2D shows the removal of the tissue growth within the stent with the current invention cutter device.
Figure 5:
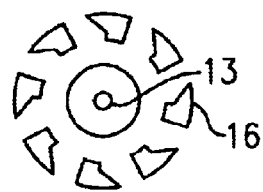
FIG. 5 is an end view of the device showing the cutter blades in the closed position.
Figure 6:
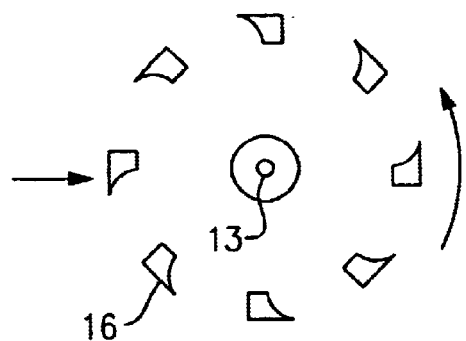
FIG. 6 is an end view of the device showing the cutter blades in the open position; and, FIG. 7 is a sectioned lumen in which a stent is present, demonstrating the rotational action of the device in removing the ingrown tissue.
Figure 7:
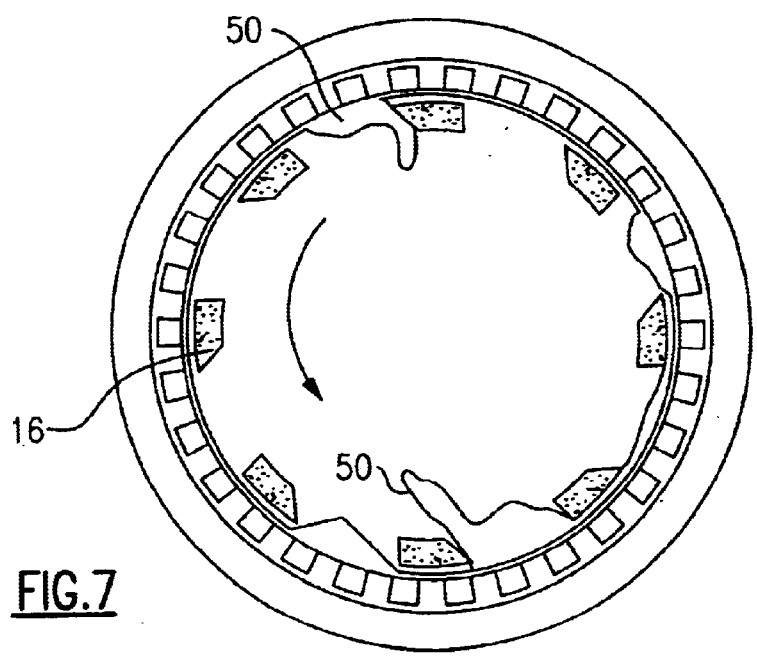

Referring to FIG. 2d, a basket 200 is deployed in spaced apart relation to the distal end of the cutter 10. The basket 200 is deployed over a guide wire by means of a sheath introducer and is deployed distally relative to the cutter 10.

Referring to FIGS. 3–7 and initially to FIG. 3, the intraluminal cutter 10 of the present invention is deployed to the target lumen over a guide wire 13. The guide wire 13 passes through the inside of the cutter 10 along its longitudinal axis 14. The cutter 10 includes a set of deformable yet resilient blades 16. The blades 16 comprise a plurality of axially deformable cutting blades that extend in the radial direction from a closed position shown in FIG. 4 to a fully expanded position shown in FIG. 3.

At the distal end 18, the blades 16 are attached to a retaining collar 19. At the proximal end 20 of the blades 16, the blades 16 are attached to tubing 22. Tubing 22 extends to an external control device 25 including a two-piece handle 26 that is operated outside of the patient by the interventionist.

A fitting 28 at the end of the tubing 22 is attached to the external control device 25. The external control device 25 includes a first portion 31 that is fixedly attached to the tubing 22 through fitting 28. Rotation of the first portion 31 rotates the tubing 22 which results in rotation of the blades 16 on cutter 10.

A second portion 34 of the external control device 25 is attached to the first portion 31. As described in greater detail below, the second portion 34 is capable of rotating and is also capable of translational movement relative to first portion 31 along the longitudinal axis 14 of the device.

A second tube 40 is fixedly attached to the second portion 34 at a first end and moves independently inside the tubing 22. The tube 40 extends through tube 22 and through an axial passageway extending through first portion 31 and connects to second portion 34. At the opposite or distal end of the tube 40 it is attached to collar 19. Accordingly, tube 22 holds one end of the blades 16 and tube 40 is disposed inside tube 22 and attaches to collar 19 which holds the opposite end of the blades 16. Tube 40 moves independently of tube 22 in the axial direction. When tube 40 is extended in the distal direction it pushes collar 19 away from the end of tube 22. The resulting force causes the blades 16 to flatten out as shown in FIG. 4. When tube 40 is pulled inward toward the end of tube 22, the cutting blades 16 expand radially as shown in FIG. 3.

The first portion 31 and second portion 34 are disposed so that in a first position the second portion 34 cannot be moved away from the first portion 31 in the axial direction. In this configuration, the portions 31, 34 are held together so that the blades 16 stay in a set position, and the portions 31, 34 may be rotated in unison to operate the cutter 10. In a second configuration, the first and second portion 31, 34 are released by rotating them relative to one another to open a mechanical interlock to allow the second portion 34 to be moved away from the first portion 31 in the axial direction to adjust the position of the blades 16.

As shown the first portion 31 carries a shaft 100 with a groove 103 disposed therein, and the second portion 34 has a bore 106 defined therein with a notch 109 extending from the inside wall. The two portions 31, 34 are mechanically interlocked by means of the notch 109 on the inner wall on the inside of the second portion 34. The notch 109 engages with the groove 103 disposed along a portion of the circumference inside the shaft 100 on the first portion 31. Rotation of the second portion 34 relative to the first portion 31 causes the notch 109 to rotate to a portion of the shaft where the groove no longer obstructs the notch 109. At this position, the second portion 34 may be moved in the axial direction away from the first portion 31. Additional grooves may be added so that the second portion can be moved into another position and then rotated back into locking engagement. As a result the blades 16 can be adjusted and then the two portions 31, 34 can be locked together. The mechanical interlock between the first and second portions 31, and 34 is one example of a suitable interlock. The shaft 100 and bore 106 and the notches 109 and grooves 103 can be arranged on the portions 31, 34 in numerous-other ways to accomplish the same function as will be obvious to those of ordinary skill in the art. The important point is that the two portions 31, 34 are capable of coupling and then uncoupling to allow axial movement of the second portion 34 relative to the first portion 31. The second portion 34 may be moved axially relative to the first portion 31 and then locked into a new position by means of rotation of the second portion 34 to engage the mechanical interlock.

In use, the cutter 10 is inserted in the closed position through a lumen. The cutter 10 is passed over the guide wire 13 through the lumen which could be a bile duct. The cutter 10 is threaded through the lumen over the guide wire 13 to arrive at the clogged stent. The cutter 10 is then actuated by rotating the second portion 34 relative to the first portion 31 and then moving the second portion 34 away from the first portion 31 in the axial direction to open the blades 16. After the blades 16 are opened to the appropriate diameter, the second portion 34 is rotated relative to the first portion 31 to lock the blades into position by means of the cooperating notches 109 and grooves 103. The cutter 10 is then operated by rotating the blades 16 by means of rotating the handle 26. The handle may be rotated manually or it may be rotated by an automatic drive (not shown). When the handle 26 is rotated to operate the blades 16, both portions 31, 34 rotate in unison so that the blades 16 do not become twisted.

The rotating blades 16 remove the ingrown tissue 43 from the inside of the stent. As a result and with minimal trauma, the ingrowth is removed from the stent.

In the TIPS application, the particles of tissue that are removed by the cutter 10 can be captured by the basket mesh, included in the system and removed through the introducer sheath. It is not necessary to employ a protection mechanism for the biliary stent application because in the biliary application, the fragments and debris will migrate into the bowel loops of the patient without harm.

While the invention has been described in connection with certain embodiments, it is not intended to limit the scope of the invention to the particular forms set forth, but, on the contrary, it is intended to cover such alternatives, modifications, and equivalents as may be included within the spirit and scope of the invention as defined by the appended claims.

What is claimed is:

1. An intraluminal cutting system, comprising:

a guide wire;

a first tubular member having a longitudinal axis, a distal end, and a proximal end, the tubular member having an axially disposed opening sized to receive the guide wire;

a plurality of resilient blades having a first end and a second end, the first end connected to the distal end of the first tubular member;

a retaining collar attached to the second end of the blades;

a second tubular member having a proximal end and a distal end, the distal end being attached to the retaining collar; and, an external control device having a handle including a first portion and a second portion, the first portion connected to the proximal end of the first tubular member, the second portion connected to the proximal end of the second tubular member, the second portion capable of being moved axially relative to the first portion to deploy the blades;

wherein the first portion comprises a shaft having a groove defined therein, the groove oriented substantially perpendicular to the longitudinal axis, the second portion having a bore with an inner wall having a notch thereon, the notch disposed such that rotation of the second portion in a first direction causes the notch to rotate into a first position where it is prevented from moving in the axial direction by a ledge bordering the notch and such that further rotation in the first direction causes the first and second portion to rotate in unison, the notch disposed such that rotation of the second portion in a second direction opposite the first direction causes the notch to move out of the groove such that the second portion is capable of axial movement relative to the first portion.

2. The cutting system of claim 1, further comprising a basket for trapping particles released by the blades, the basket deployed over the guide wire and positioned downstream from the distal end of the first tubular member.

3. A method for cutting ingrowth from a stent, comprising:

providing a guide wire, a tubular member having a longitudinal axis, a distal end, and a proximal end, the tubular member having an axially disposed opening sized to receive the guide wire, a plurality of resilient blades having a first end and a second end, the first end connected to the distal end of the tubular member, a retaining collar attached to the second end of the blades, a second tubular member having a proximal end and a distal end, the distal end being attached to the retaining collar; an external control device having a handle including a first portion and a second portion, the first portion connected to the proximal end of the tubular member, the second portion connected to the proximal end of the second tubular member, the second portion capable of being moved axially relative to the first portion to deploy the blades, wherein the first portion comprises a shaft having a groove defined therein, the groove oriented substantially perpendicular to the longitudinal axis, the second portion having a bore with an inner wall having a notch thereon, the notch disposed such that rotation of the second portion in a first direction causes the notch to rotate into a first position where it is prevented from moving in the axial direction by a ledge bordering the notch and such that further rotation in the first direction causes the first and second portion to rotate in unison, the notch disposed such that rotation of the second portion in a second direction opposite the first direction causes the notch to move out of the groove such that the second portion is capable of axial movement relative to the first portion;

deploying the guide wire through the vasculature to the target lumen;

deploying the cutting system over the guide wire to the target lumen;

opening the cutting system by rotating the second portion relative to the first portion to cause the blades to expand in the radial direction; and, rotating the handle so that the blades rotate inside the target lumen such that the ingrowth is trimmed from inside the lumen.

4. The method of claim 3, further comprising deploying a basket over the guide wire in spaced apart relation to the distal end of the first tubular member.

5. The method of claim 3, wherein the target lumen is a TIPS shunt.

6. The method of claim 3, wherein the target lumen is a biliary stent.

* * * * *